(12) United States Patent
Lee et al.

(10) Patent No.: US 6,964,730 B2
(45) Date of Patent: Nov. 15, 2005

(54) PURIFICATION APPARATUS AND METHOD

(75) Inventors: Kyung Hoon Lee, Seoul (KR); Jeong Dae Seo, Gyeonggi-do (KR); Hyoung Yun Oh, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 10/671,549

(22) Filed: Sep. 29, 2003

(65) Prior Publication Data
US 2004/0069609 A1 Apr. 15, 2004

(30) Foreign Application Priority Data
Sep. 30, 2002 (KR) ............... 10-2002-0059519

(51) Int. Cl.⁷ .................................................. B01D 3/00
(52) U.S. Cl. ..................... 203/41; 202/161; 202/183; 202/202; 203/98; 203/DIG. 2; 210/664; 422/101; 422/291
(58) Field of Search ..................... 202/161, 83, 202, 202/183, 184; 203/DIG. 2, 100, 98, 41; 159/906; 422/101, 291; 210/664, 667, 500.29

(56) References Cited

U.S. PATENT DOCUMENTS

| | | | |
|---|---|---|---|
| 2,733,135 A | | 1/1956 | Huckabay ..................... 436/31 |
| 4,255,386 A | * | 3/1981 | Schachter et al. ........... 422/101 |
| 4,265,860 A | * | 5/1981 | Jennings et al. ............. 422/280 |
| 4,861,561 A | | 8/1989 | Pritchard ...................... 422/116 |
| 4,920,792 A | | 5/1990 | DiFoggio ......................... 73/153 |
| 5,147,538 A | * | 9/1992 | Wright et al. ............. 210/198.2 |
| 5,776,317 A | * | 7/1998 | Spring et al. ................ 202/168 |
| 6,790,318 B2 | * | 9/2004 | Lai et al. ...................... 202/169 |

FOREIGN PATENT DOCUMENTS

| | | |
|---|---|---|
| DE | 3614556 A1 | 11/1987 |
| JP | 61-127631 | 6/1986 |

OTHER PUBLICATIONS

J. Org. Chem. 1992, 57, 3254–3256.
Korean Office Action.

* cited by examiner

Primary Examiner—Virginia Manoharan
(74) Attorney, Agent, or Firm—Fleshner & Kim, LLP

(57) ABSTRACT

Disclosed is a purification apparatus and method. The purification apparatus includes: a mobile phase distillation part for distilling a mobile phase; a mobile phase liquefaction part for liquefying the distilled mobile phase; and a purification part disposed between the mobile phase distillation part and the mobile phase liquefaction part, for mixing the mobile phase liquefied at the mobile liquefaction part with to-be-purified material, removing impurities from the mixture through a bonded phase, and sending the impurity-removed purified material to the mobile phase distillation part.

18 Claims, 1 Drawing Sheet

PURIFICATION APPARATUS AND METHOD

This application claims the benefit of the Korean Application No. P2002-59519 filed on Sep. 30, 2003, which is hereby incorporated by reference.

BACKGROUND OF THE INVENTION

1. Field of the Invention

The present invention relates to a purification apparatus, and more particularly, to an apparatus and method for purifying organic material.

2. Discussion of the Related Art

In general, purification of organic material from a mixture is performed by a recrystallization process, a chromatography process and a sublimation process.

In the recrystallization process, a solid organic material is dissolved in an organic solvent to be made in a supersaturated state and the supersaturated organic material is then cooled, so that pure substances are separated in a crystalline state and impurities are left in the solvent.

In the chromatography process, a polarity difference of a mixture is utilized. In other words, a mixture containing impurities passes through a bonded phase with a high polarity, thereby separating pure substances.

The sublimation process is used to separate substances having a high difference in the melding point.

In other words, a mixture is heated up to a melting point and nitrogen of mobile phase is introduced into the heated mixture to thereby separate pure substances.

However, the aforementioned purification processes of organic material needs a high temperature and a lot of time depending on the materials for purification.

Accordingly, the purification process of organic material using a high temperature may cause the decomposition of the organic material.

Also, the sublimation process has a disadvantage in that if impurities are completely removed, the recrystallization process or the chromatography process should be performed to remove the impurities.

SUMMARY OF THE INVENTION

Accordingly, the present invention is directed to a purification apparatus and method of an organic material that substantially obviate one or more problems due to limitations and disadvantages of the related art.

An object of the present invention is to provide a purification apparatus and method of an organic material capable of purifying pure substance simply and easily.

Another object of the present invention is to provide a purification apparatus and method of an organic material having a superior substance purification performance.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a purification apparatus includes: a mobile phase distillation part for distilling a mobile phase; a mobile phase liquefaction part for liquefying the distilled mobile phase; and a purification part disposed between the mobile phase distillation part and the mobile phase liquefaction part, for mixing the mobile phase liquefied at the mobile liquefaction part with to-be-purified material, removing impurities from the mixture through a bonded phase, and sending the impurity-removed purified material to the mobile phase distillation part.

The mobile phase distillation part includes: a flask containing the mobile phase therein; and a heater for generating heat so as to distill the mobile phase. The mobile phase is an organic solvent.

The mobile phase liquefaction part is a reflux condenser.

The purification part comprises: a cellulose or silica thimble for mixing the mobile phase liquefied at the mobile phase liquefaction part with the to-be-purified material; a bonded phase for removing impurities from the mixture of the cellulose or silica thimble; and a soxhlet for sending the purified material, in which the impurities are removed by the bonded phase, to the mobile phase distillation part.

The bonded phase is at least one or two or more selected from the group consisting of silica gel, alumina, celite and activated carbon. Alternatively, the bonded phase further comprises a predetermined thickness of a sand layer formed on upper and lower surfaces thereof.

The soxhlet sends the impurity-removed purified material to the mobile phase distillation part through a capillary tube. An inlet of the capillary tube is filled with cotton such that only the purified material passes.

Here, the capillary tube has a predetermined region that is larger in diameter than other regions.

In another aspect of the present invention, a purification apparatus includes: a flask for containing an organic solvent therein; a heater for distilling the organic solvent; a condenser for liquefying the distilled organic solvent; a cellulose thimble disposed at a lower portion of the condenser, for mixing the organic solvent liquefied at the mobile phase liquefaction part with to-be-purified organic material; a bonded phase disposed at a lower portion of the cellulose or silica thimble, for removing impurities from the mixture of the cellulose or silica thimble; and a soxhlet for sending the purified material, in which the impurities are removed by the bonded phase, to the flask.

In a further aspect of the present invention, there is provided a purification method using a purification apparatus having a mobile phase distillation part; a mobile phase liquefaction part; and a purification part disposed between the mobile phase distillation part and the mobile phase liquefaction part, for removing impurities of to-be-purified material. The method includes the steps of: distilling a mobile-phase solvent; liquefying the distilled solvent; mixing the liquefied solvent with the to-be-purified material; removing impurities from the mixture using the bonded phase; sending the purified material, in which the impurities are removed by the bonded phase, to the mobile phase distillation part; and extracting the purified material from the mobile phase distillation part.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawing.

DETAILED DESCRIPTION OF THE INVENTION

Figure 1:
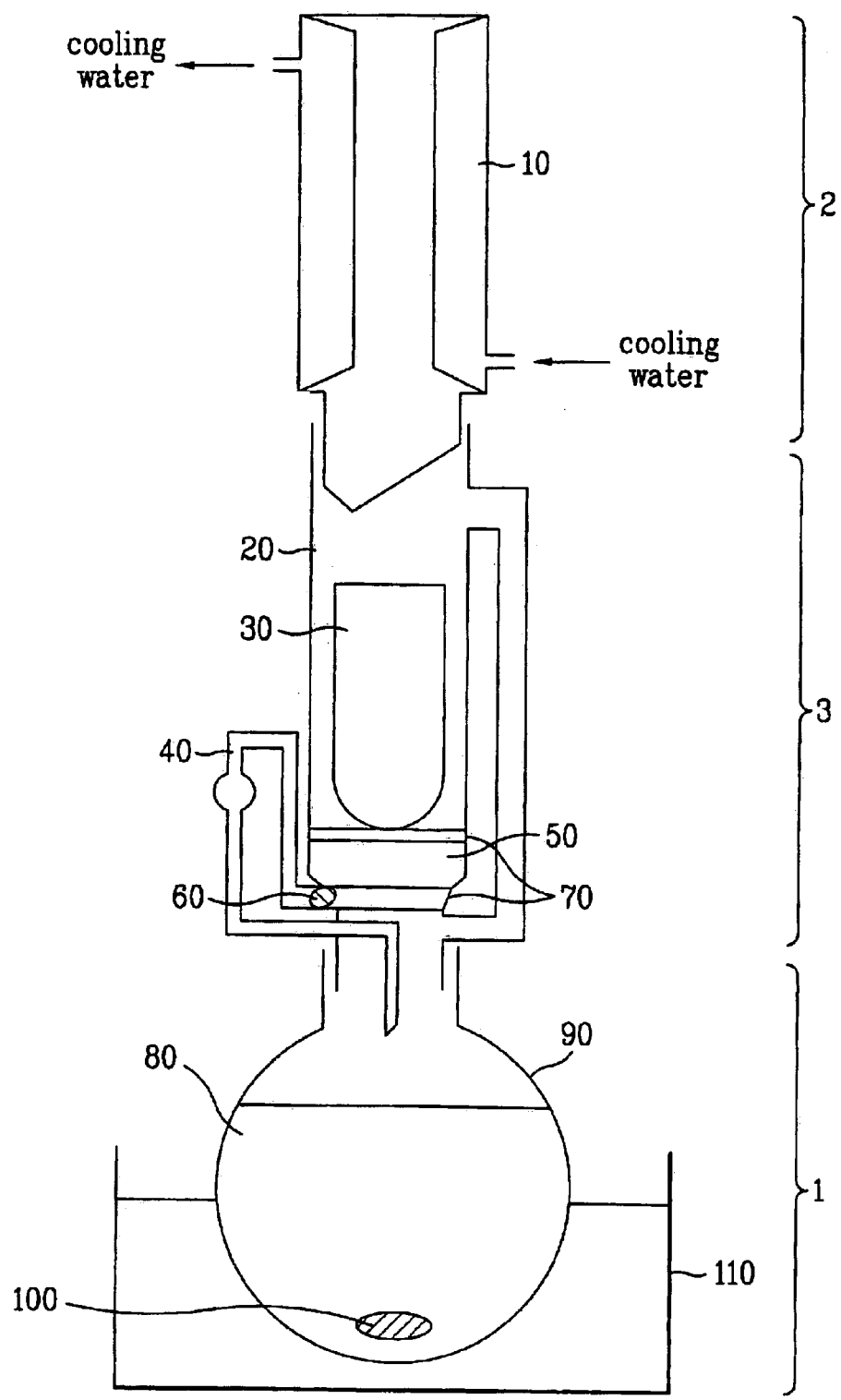
FIG. 1 is a view of a purification apparatus according to the present invention.

Reference will now be made in detail to the preferred embodiments of the present invention to achieve the objects, with examples of which are illustrated in the accompanying drawings. Wherever possible, the same reference numbers will be used throughout the drawings to refer to the same or like parts.

FIG. 1 is a view of a purification apparatus according to the present invention.

Referring to FIG. 1, a purification apparatus of the present invention includes a mobile phase distillation part 1, a mobile phase liquefaction part 2 and a purification part 3 disposed therebetween.

The mobile phase distillation part 1 distills a mobile phase, and the mobile phase liquefaction part 2 liquefies the distilled mobile phase. The purification part 3 is disposed between the mobile phase distillation part 1 and the mobile phase liquefaction part 2. The purification part 3 mixes the mobile phase liquefied at the mobile liquefaction part 2 with to-be-purified material, and impurities are removed from the mixture by using a bonded phase. Thereafter, the purification part 3 sends the impurity-removed, or purified material to the mobile phase distillation part 1.

The mobile distillation part 1 is provided with a flask 90 containing mobile-phase organic solvent 80 and a heater 110 generating heat so as to distill the mobile-phase organic solvent 80. An agitation magnet 100 is disposed at a bottom of the flask 90.

The mobile phase liquefaction part 2 is constructed with a reflux condenser 10.

Here, the reflux condenser 10 liquefies the distilling organic solvent 80 through cooling water and sends it to a cellulose or silica thimble 30.

The purification part 3 is generally configured to have the cellulose or silica thimble 30, a bonded phase 50 and a soxhlet 20.

The cellulose or silica thimble 30 containing solid organic material to be purified mixes the organic solvent 80 liquefied at the reflux condenser 10 with the solid organic material to be purified, thereby dissolving the solid organic material.

The bonded phase 50 removes impurities from the mixture contained in the cellulose or silica thimble 30.

The bonded phase 50 can be any one selected from the group consisting of silica gel, alumina, celite and activated carbon. A sand layer 70 having a predetermined thickness can be formed at upper and lower portions of the bonded phase 50.

The soxhlet 20 sends the purified material, in which the impurities are removed by the bonded phase, to the flask 90 of the mobile phase distillation part 1.

Here, the soxhlet 20 sends the impurity-removed purified material to the flask 90 through a capillary tube 40.

An inlet of the capillary tube 40 is closed up with cotton 60 so as to pass only the purified material.

A method for purifying the organic material using the purification apparatus constructed as above will be described below.

As shown in FIG. 1, the soxhlet 20 is first installed in a lower portion of the reflux condenser 10, and the inlet of the capillary tube 40 of the soxhlet 20 is filled with the cotton 60 so as to prevent the bonded phase 50 such as silica gel from being exhausted through the capillary tube 40.

After laying thinly a sea sand 70 on the inlet of the capillary 40, the bonded phase 50 such as silica gel or alumina, which has high polarity, is laid to a thickness of about 3 cm on the sea sand 70.

After filling the round flask 90 with about 70 ml of methylene chloride that is the organic solvent 80, the flask 90 is packed on a lower portion of the soxhlet 20.

After putting 1 g of the organic material to be purified into the cellulose or silica thimble 30, the cellulose or silica thimble 30 is put into the soxhlet 20.

Here, the organic material used is an organic material that is not liquefied well, and it contains a metal oxide as the impurities.

Specifically, this substance cannot be removed even if a recrystallization process is used. Also, this substance is a material that impurities are generated as ever even if a sublimation process is used.

After an installation of the purification apparatus, the flask 90 containing the organic material 80 is heated to about 100° C. using the heater 110.

If so, the organic solvent 80 contained in the flask 90 is distilled and injected into the reflux condenser 10. Then, the distilled organic solvent 80 is liquefied by the reflux condenser 10.

At this time, the reflux condenser 10 liquefies the distilling organic solvent 80 using cooling water.

The liquefied organic solvent 80 is dropped into the cellulose or silica thimble 30 of the soxhlet 20.

Accordingly; the solid organic material contained in the cellulose or silica thimble 30 is dissolved by the liquefied organic solvent 80.

Then, if the organic solvent 80 and the dissolved organic material rise up to a predetermined height in the cellulose or silica thimble 30, the organic solvent 80 changes into the mobile phase, so that the mobile phase passed through the sea sand 70 and the bonded phase, which is constituted with silica gel, alumina, celite, activated carbon, etc., and is exhausted through the capillary tube 40.

At this time, the purified organic material is exhausted together. The metal oxide that is an unpurified impurity is blocked since it does not pass through the sea sand 70 and the bonded phase 50.

Here, the bonded phase 50 separates the materials using polarity difference of the mixture.

Then, the cotton installed in the inlet of the capillary tube 40 covers an opening through which the purified organic material and the organic solvent 80 are exhausted, thereby preventing silica gel, alumina, celite and activated carbon from being exhausted through the capillary tube 40.

The organic solvent 80 and the purified organic material exhausted through the capillary tube 40 flow into the flask 90, which is disposed at the lower portion and contains the organic solvent 80.

Here, the organic solvent and the purified organic material are exhausted to the flask 90 by a capillary phenomenon using a surface tension since a predetermined portion of the capillary tube 40 is formed to have a diameter larger than other portions.

If these procedures are carried out successively, the purified clear organic material floats in the flask 90 after about 12 hours.

Additionally, the metal oxide that is an impurity is filtered on the upper surface of the bonded phase 50.

Accordingly, the purified organic material can be obtained simply and easily by filtering the organic solvent 80 contained in the flask 90.

If the organic material purified in the above manner is again purified using the sublimation process, there is an advantage that a very purified organic material can be obtained.

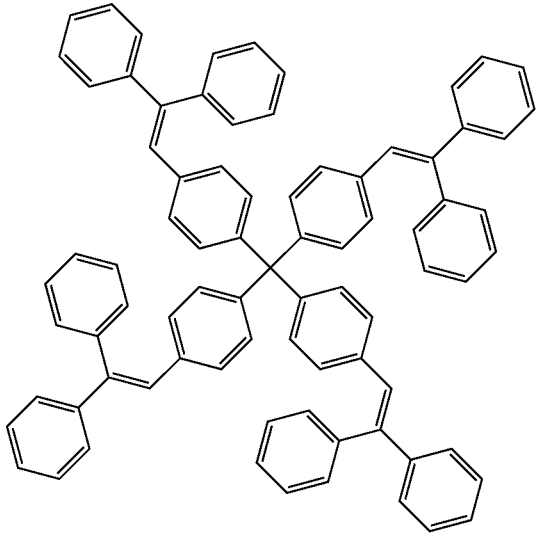

If the organic material constructed as above is purified by using the purification apparatus of the present invention, a remarkable difference is made between an organic EL device manufactured with the purified material and an organic EL device manufactured with the unpurified material.

A following Table 1 shows a difference between a case of using the purified organic material and a case of using the unpurified organic material when an organic EL device has a structure of ITO (1200 Å) CuPc (250 Å) NPD (350 Å) blue light emitting layer (200 Å) Alq3 (300 Å) LiF (5 Å) Al (1000 Å).

TABLE 1

|  | Current (mA) | Voltage (V) | Luminance (cd/m$^2$) | C.I.E. (x, y) |
|---|---|---|---|---|
| Unpurified matter | 1 | 12.0 | 66.0 | (0.214, 0.300) |
| Purified matter | 1 | 9.3 | 114.5 | (0.187, 0.228) |

As shown in Table 1, it can be seen that there is a great difference of the luminance and the chromaticity coordinate (C.I.E) between the organic material purified using the soxhlet 20 and anything else.

Accordingly, it can be seen that the organic material purification using the purification apparatus of the present invention has a superiority since the material purification using the soxhlet 20 improves a characteristic of the organic EL device.

Even solid organic materials that are not dissolved well can be purified simply and easily since the present invention use the soxhlet method and the liquid chromatography method at the same time.

As described above, the purification apparatus and method of the present invention has an excellent capability of purifying materials simply and easily.

Further, materials can be easily purified even with a small amount of organic solvent.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A purification apparatus comprising:
    a mobile phase distillation part for distilling a mobile phase;
    a mobile phase liquefaction part for liquefying the distilled mobile phase; and
    a purification part disposed between the mobile phase distillation part and the mobile phase liquefaction part,
    wherein the purification part comprises:
    a cellulose or silica thimble for mixing the mobile phase liquefied at the mobile phase liquefaction part with to-be-purified material;
    a bonded phase for removing impurities from the mixture; and
    a soxhlet for sending purified material, in which the impurities are removed by the bonded phase, to the mobile phase distillation part.

2. The purification apparatus of claim 1, wherein the mobile phase distillation part comprises:
    a flask containing the mobile phase therein; and
    a heater for generating heat so as to distill the mobile phase.

3. The purification apparatus of claim 2, wherein the mobile phase is an organic solvent.

4. The purification apparatus of claim 1, wherein the mobile phase liquefaction part is a reflux condenser.

5. The purification apparatus of claim 1, wherein the bonded phase is at least one selected from the group consisting of silica gel, alumina, celite and activated carbon.

6. The purification apparatus of claim 1, wherein the bonded phase further comprises a predetermined thickness of a sand layer formed on upper and lower surfaces thereof.

7. The purification apparatus of claim 1, wherein the soxhlet sends the impurity-removed purified material to the mobile phase distillation part through a capillary tube.

8. The purification apparatus of claim 7, wherein an inlet of the capillary tube is filled with cotton such that only the purified material passes.

9. A purification apparatus comprising:
    a flask for containing an organic solvent therein;
    a heater for distilling the organic solvent;
    a condenser for liquefying the distilled organic solvent;
    a cellulose or silica thimble disposed at a lower portion of the condenser, for mixing the organic solvent liquefied at the mobile phase liquefaction part with to-be-purified organic material;
    a bonded phase disposed at a lower portion of the cellulose or silica thimble, for removing impurities from the mixture; and
    a soxhlet for sending the purified material, in which the impurities are removed by the bonded phase, to the flask.

10. The purification apparatus of claim 9, wherein the condenser is a reflux condenser.

11. The purification apparatus of claim 9, wherein the bonded phase is at least one selected from the group consisting of silica gel, alumina, celite and activated carbon.

12. The purification apparatus of claim 9, wherein the bonded phase further comprises a predetermined thickness of a sand layer formed on upper and lower surfaces thereof.

13. The purification apparatus of claim 9, wherein the soxhlet sends the impurity-removed purified material to the flask through a capillary tube.

14. The purification apparatus of claim 13, wherein an inlet of the capillary tube is filled with cotton such that only the purified material passes.

15. A purification method using a purification apparatus having a mobile phase distillation part; a mobile phase liquefaction part and a purification part disposed between the mobile phase distillation part and the mobile phase liquefaction part, for removing impurities of to-be-purified material, the method comprising the steps of:

distilling a mobile-phase solvent;

liquefying the distilled solvent;

mixing the liquefied solvent with the to-be-purified material using a cellulose or silica thimble;

removing impurities from the mixture using a bonded phase;

using a soxhlet to send the purified material, in which the impurities are removed by the bonded phase, to the mobile phase distillation part; and extracting the purified material from the mobile phase distillation part.

16. The purification method of claim 15, wherein the bonded phase is at least one selected from the group consisting of silica gel, alumina, celite and activated carbon.

17. The purification method of claim 15, wherein the purified material is moved to the mobile phase distillation part by a capillary phenomenon having a difference of a surface tension.

18. The purification method of claim 15, wherein the purified material is purified by a polarity difference of the mixture.

* * * * *